United States Patent [19]

Bjorndal et al.

[11] Patent Number: 4,676,650
[45] Date of Patent: Jun. 30, 1987

[54] INSPECTION DEVICE

[75] Inventors: Paul M. Bjorndal, Clifton; Julius Z. Knapp, Somerset; John C. Zeiss, Glen Ridge, all of N.J.

[73] Assignee: Schering-Plough Corporation, Kenilworth, N.J.

[21] Appl. No.: 553,012

[22] Filed: Nov. 18, 1983

[51] Int. Cl.⁴ .................. G01N 21/90; H04N 7/18
[52] U.S. Cl. .................................. 356/427; 358/106
[58] Field of Search ..................... 356/427; 358/106

[56] References Cited

U.S. PATENT DOCUMENTS 3,966,332  6/1976  Knapp et al. ................... 250/223 X
4,087,184  5/1978  Knapp et al. ................... 356/240 X
4,402,612  9/1983  Alexander et al. ............. 358/106 X Primary Examiner—Michael R. Lusignan
Attorney, Agent, or Firm—John J. Maitner; Stephen I. Miller; James R. Nelson

[57] ABSTRACT

A method and apparatus for lighting a container which is to be inspected for particulate contamination comprising a first lighting means consisting of two angularly displaced light beams which create an angular shadow zone, a second lighting means of significantly lower intensity than said first lighting means and positioned intermediate the two light beams and a viewing means positioned in the shadow zone.

23 Claims, 4 Drawing Figures

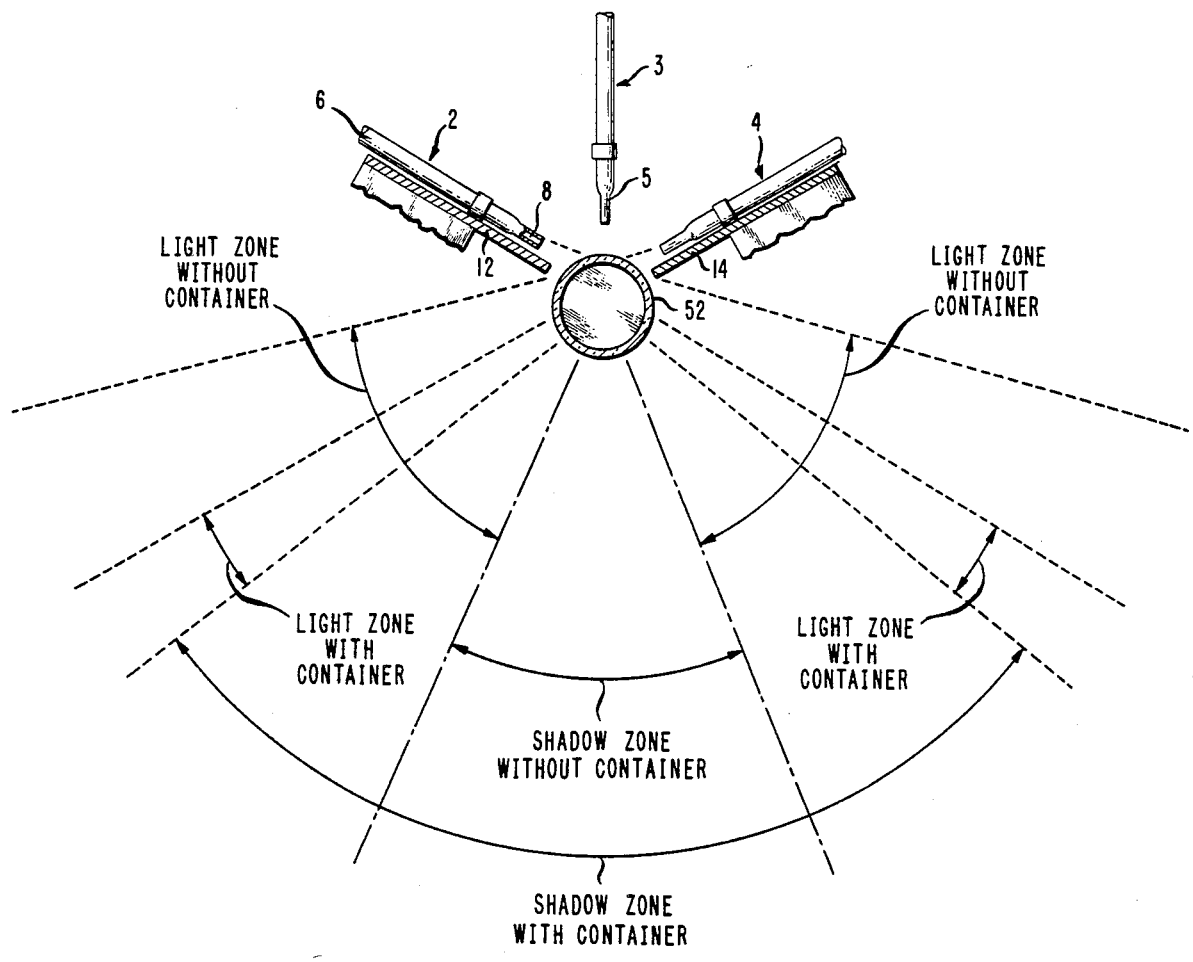

INSPECTION DEVICE

This invention relates to a method and apparatus for inspecting liquids for particulate contaminates, especially solutions for parenteral injection. Particularly this invention is an improvement over the shadow zone lighting technique described in U.S. Pat. Nos. 3,627,423; 3,914,058; 3,966,332 and 4,087,184, all of which are herein incorporated by reference.

Pharmaceutical solutions for parenteral injection are prepared and packaged with precautions to prevent particulate contamination, however, despite the precautions taken, particulate contamination does occur. Since particulates can be dangerous or even lethal if injected into the patient, an inspection of each container, after it is filled and sealed, is mandatory.

The method and apparatus of this invention is especially suited to the inspection of liquid in transparent containers, particularly blow-molded hermetically-sealed glass vials and ampuls.

Various attempts have been made for inspecting liquids for particulate contamination. Such arrangements have included detection of the particles as they pass between a direct illuminating means and a detection unit aligned with the illuminating means. Such arrangements are difficult to adjust or calibrate and oftentimes are responsive only to a portion of the particulates encountered. For the most part, these prior art systems have relied on the amplitude modulation of light passing from the illuminating source to the detection unit to indicate particulate contamination. Unfortunately, such light modulation does not accurately indicate particle size since the signal's amplitude is also affected by the optical transmission of the particle. In many such systems, the detection unit and illuminating source are positioned at opposite sides of the container, and perpendicular to the movement of the contaminating particles in the container when such container and contents are rotated. This alignment makes it difficult to detect low contrast particles and those particles floating on the surface of the solution or resting on the bottom of the container. It is, however, well suited to the detection of dark, opaque or high contrast particulates in the body of the liquid.

In another prior art device, the light source is directed at the bottom of the container with the viewing means at right angles to the rotational axis of the container. Such systems are well suited to the detection of low contrast particulates in the body of the liquid but lack sensitivity to detect dark particulates. Unfortunately, the meniscus and container bottom often create glare signals in these systems, and glare generates saturation level signals blocking the detection of small particles. Because of the difficulties and lack of overall security of such methods and apparatus, the pharmaceutical industry often resorts to visual inspection by operators against a white and black background. Such visual inspection is slow, time consuming, costly and subject to human ability, judgement, fatigue and error. Also, even under the most ideal of inspection conditions, only relatively large particles can be detected by the human eye.

In the lighting system described in U.S. Pat. No. 3,627,423, the viewing means is located in a shadow zone. Such a system is well suited to the detection of most contaminating particles, however, it oftentimes will miss the detection of small black particles.

We have found that a highly acurate inspection system which detects the full range of low contrast, black and opaque particles is achieved by incorporating an auxiliary, direct, low-intensity lighting means into the system described in U.S. Pat. No. 3,627,423. This direct lighting means is positioned between the two angularly disposed light sources disclosed in the patent.

In the method and apparatus of the instant invention, the container to be inspected is illuminated from both a direct low-intensity (i.e. low electrical wattage) light source disposed on the viewing axis. The ratio of the image plane intensity of the direct light source to the image plane intensity of the side light sources is in the range of 3:1 to 1:3, preferably 3:2 to 2:3. Most preferably, the image plane intensities of the two light sources are approximately equal. In a 2 ml pharmaceutical container, the image plane intensity of the two light sources can be approximately equalized if the ratio of the electrical wattage of the side light sources to the back light is 1000:1 to 100:1, most preferably 500:1. Single or multiple optical glass fiber bundles exposed, at one end, to a common light source and arranged in columns at opposite sides of the viewing axis of the sensing device have been found to be especially suited for the angular illumination. The combination of direct and angular light sources provides secure detection capability for the full range of particulate size from low contrast to opaque and black particulates. For example, the inspection system described in U.S. Pat. 4,087,184 would achieve Rejection Zone Efficiencies of approximately 90%. Incorporation of the direct light into this system results in a Rejection Zone Efficiency of over 98%. Rejection Zone Efficiency refers to the average probability of rejecting those containers having serious particulate contami- nation.

The container to be inspected is positioned between the light sources and the sensing device. The light rays emanating from the side sources are not directed toward the sensing device, but rather, are directed at the container so that the light beams intersect in the container. The inner wall of the container reflects the light into the liquid so that substantially all of the liquid is illuminated. The angles at which the side light sources are directed at the container are adjusted to create a shadow zone radiating outwardly from the container. This shadow zone results even with the incorporation of the low intensity direct light source described herein. The sensing or viewing device is situated in this angular shadow zone. Preferably, the side light sources are shielded and positioned so that the image of the light sources reflected in the glass wall of the container do not appear on the sensing device.

The sensing device may be a camera as disclosed in U.S. Pat. No. 3,627,423 or any type of electro-optical transducer which produces an electrical response proportional to the varying light intensity of the image focused on it. A suitable electro optic transducer is described in U.S. Pat. No. 4,087,184. The viewing axis is preferably perpendicular to the container axis, however, this axis can be inclined relative to the vertical axis of the container provided that the upper surface and bottom of the container, as well as the solution therebetween, is within the viewing area of the sensing device.

The container to be inspected is first positioned between the light sources and the viewing means, then rotated and stopped before inspection. This rotation of the container is at sufficient speed and sufficient duration to rotate the liquid and any particles therein but is below the speed that will cause cavitation and bubbling of the liquid. Rotation of the liquid and any particles therein causes the image of the particles to move across the camera or unit detection elements. Such movement is distinguished from stationary images caused by flaws or markings in the container walls and dust particles that may be on the outside of the container. In an automatic inspection device, the resulting image is picked up by the sensing means and transmitted to an image analyzer. Particle size signals are then compared to stored accept-reject criteria based upon pulse-time duration distributions. The criteria chosen is arbitrarily selected and controlled. For purposes of inspecting parenteral solutions a maximum particle size of thirty five microns, which is below the size of particles detectable by the unaided human eye, has been found to be acceptable.

The instant invention will be more fully understood from the following description and appended drawings of an illustrative embodiment in which FIG. 1 is a top plan view of the apparatus in front elevation view;

FIG. 4 is an enlarged view showing, schematically, the passage of the light through the container and liquid.

Figure 1:
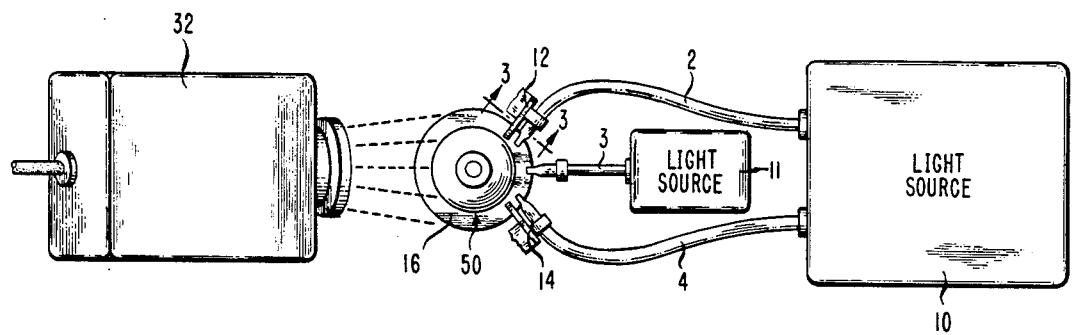
Figure 3:
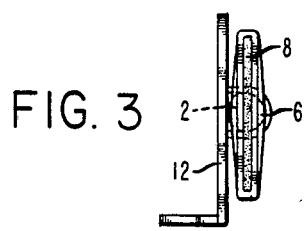
FIG. 3 is a sectional view taken at 3-3, FIG. 1.

Referring to the drawings, cables 2, 4, each having an outer protective shield 6 and an optical glass fiber bundle 8 within shield 6 are connected, at one of their ends, to a light source 10. Cable 3 having a similar optical glass fiber bundle 5 is connected at one of its ends to a second light source 11. The optical bundles of cables 2 and 4 are fixedly mounted, at their opposite ends, behind baffles 12 and 14. The ends of cables 2 and 4 are open and receive light from source 10. Cable 3 is similiarly open to receive light from light source 11. Any light source having an intensity sufficient to illuminate the liquid and particles and compatable with the viewing means may be employed. A 150 Watt 21 Volt, incandescent light, for example General Electric type EKE, has been found suitable for light source 10. A vertically aligned array of Light Emitting Diodes (LED) having approximately 10 to 20 milliwatts per diode has been found suitable for light source 11.

Figure 2:
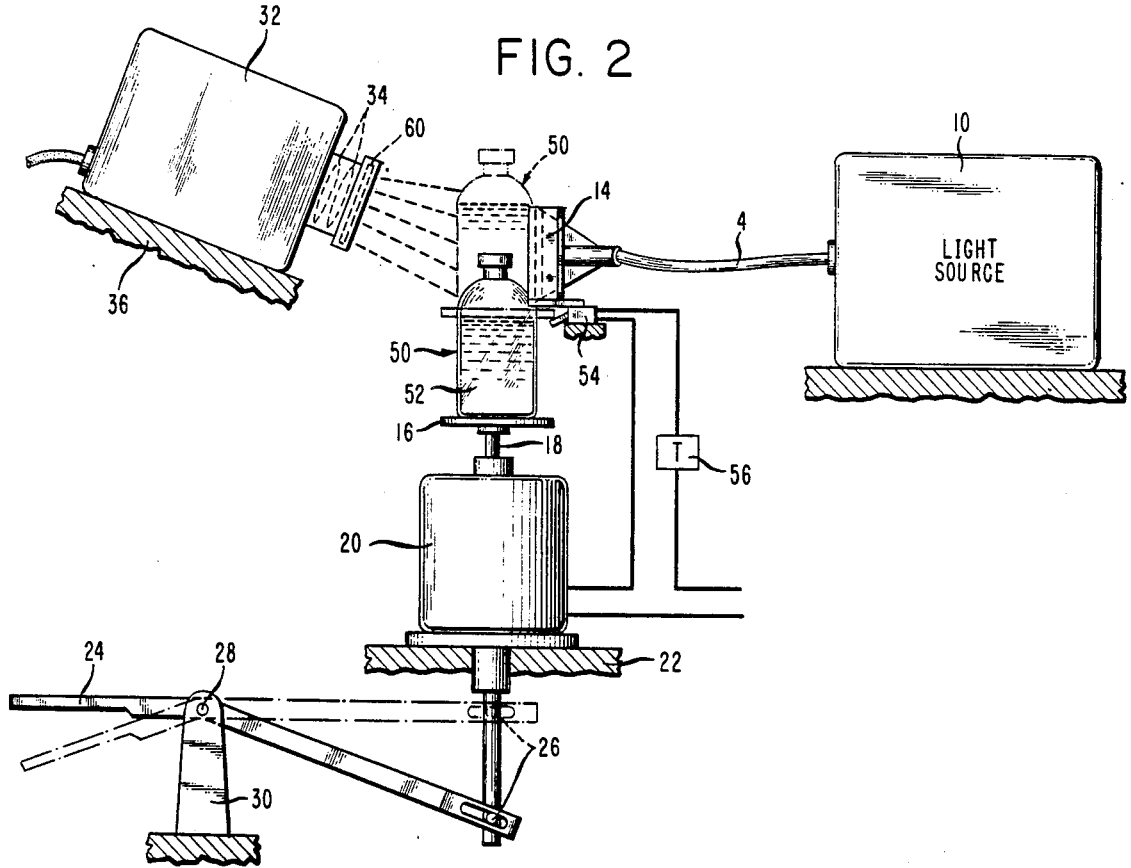
FIG. 2 is a side elevational view of the apparatus of FIG. 1.

FIG. 2 shows turntable 16 mounted on a shaft 18 which is driven by a motor 20. Motor 20 is on a support 22 and is movable, vertically through lever 24, pivot 28, and fixed support 30. Turntable 16 is elevated from its solid line position to its dotted line position by depressing lever 24. As container 50 and turntable 16 reach the dotted line position, micro-switch 54 is closed and motor 20 is actuated for a pre-set time interval as determined by timer 56. The speed and time of rotation is sufficient to cause solution 52 and any particles therein to rotate but is below the speed of cavitation, bubbling and entrapment of air in the solution.

Camera 32, having a viewing lens 34, is mounted on fixed support 36 so that the viewing lens 34 is tilted slightly downwardly toward the dotted line viewing position. Automatic viewing means as illustrated in U.S. Pat. Nos. 3,966,332 and 4,087,184 can be substituted for camera 32.

In the method and apparatus of the instant invention, the surface of any particles in the solution is illuminated both by directed and reflected light as illustrated in FIG. 4. The beams of light from cables 2, 3, and 4 pass through the wall of container 50 and intersect in solution 52.

In a preferred embodiment for inspecting 2 ml parenteral containers the width of the fiber optic bundles 5 and 8 is from 5-75%, preferably 10-30%, of the diameter of the container. Light source 10 has an intensity of 40-80 watts. Light source 11 has a preferred intensity of 8-16 milliwatts per diode in vertically aligned 5-12 diode array, most preferably a 7 diode array. In a larger container the number of diodes can be increased. The angle between light sources 2 and 4 is preferably 30-60 degrees such that a shadow zone of approximately 20-40 degrees is achieved. The ratio of the wattage of light source 10 to light source 11 is from approximately 1000:1 to 100:1, preferably about 500:1.

The terms and expressions which have been employed are used as terms of description and not of limitation, and there is no intention in the use of such terms and expressions of excluding any equivalents of the features shown and described or portions thereof, but it is recognized that various modifications are possible.

WHAT IS CLAIMED IS:

1. A method for inspecting a liquid-filled transparent container for foreign particles in the liquid com- prising:
    a. placing the container at an inspection station,
    b. rotating said liquid about an axis while holding said container stationary,
    c. illuminating said container with a first lighting means comprising two light beams which intersect within said liquid and delineate an angular shadow zone radiating outwardly from said container,
    d. illuminating said container with a second lighting means which is positioned intermediate the two light beams of said first lighting means, said second lighting providing a light zone within said shadow zone and means having a lower intensity than said first lighting means,
    e. viewing said container with a viewing means positioned in said shadow zone of the first lighting means and within the light zone of the second lighting means to detect the presence of foreign particles.

2. A method as in claim 1 wherein the ratio of the intensity of said first light means to said second lighting means is from 100:1 to 1000:1.

3. A method as in claim 2 wherein said ratio is 500:1.

4. A method as in claim 1 wherein said first lighting means comprise fiber optic bundles having a width of from about 5 to about 75 percent of the diameter of said container.

5. A method as in claim 4 wherein said fiber optic bundles have a width of from about 10 to about 30 percent of the width of the diameter of said container.

6. A method as in claim 1 wherein said second lighting means comprises an array of light emitting diodes.

7. A method as in claim 6 wherein each diode has an intensity of 8 to 16 milliwatts.

8. A method as in claim 7 wherein said container is a 2 ml parenteral package and said array comprises 7 diodes.

9. A method as in claim 1 wherein the angle formed at said container between the intersection of the two light beams of said first lighting means is in the range of 30 to 60 degrees.

10. A method as in claim 1 wherein said second lighting means is positioned on the viewing axis of said viewing means.

11. A method as in claim 1 wherein the ratio of the image plane intensity of the first lighting means to the second lighting means is in the range of 3:1 to 1:3.

12. A method as in claim 11 wherein said ratio is in the range of 3:2 to 2:3.

13. A method as in claim 12 wherein said image plane intensities are approximately equal.

14. A system for inspecting a liquid-filled container for particulate contamination comprising:
   a. a first lighting means directed at said container, said first lighting means comprising at least two light beams directed at said container, said light beams intersecting within said liquid and delineating an angular shadow zone radiating outwardly from said container,
   b. a second lighting means intensity than said first lighting means and positioned intermediate said two light beams to provide a light zone within said shadow zone,
   c. a viewing, means positioned within said shadow zone and said light zone to detect the presence of foreign particles in the liquid.

15. A system as in claim 14 wherein the ratio of the wattage of said first lighting means to said second lighting means is from 1000:1 to 100:1.

16. A system as in claim 15 wherein said ratio is about 500:1.

17. A system as in claim 14 wherein said first lighting means is comprised of fiber optic bundles having a width of from about 5 to about 75 percent of the diameter of the container to be inspected.

18. A system as in claim 14 wherein said second lighting means comprises a vertical array of light emitting diodes.

19. A system as in claim 18 wherein said array comprises 5 to 10 diodes.

20. A system as in claim 19 wherein said array comprises 7 diodes.

21. A system as in claim 19 wherein each of said diodes has an intensity of from 8 to 16 milliwatts.

22. A system as in claim 14 wherein the angle formed at said container between the intersection of said two light beams of said first lighting means is between 30 and 60 degrees.

23. A system as in claim 22 wherein said second lighting means is positioned on the viewing axis of said viewing means.

* * * * *

UNITED STATES PATENT AND TRADEMARK OFFICE
CERTIFICATE OF CORRECTION

PATENT NO. : 4,676,650

DATED : June 30, 1987

INVENTOR(S) : Paul M. Bjorndal et al.

It is certified that error appears in the above-identified patent and that said Letters Patent are hereby corrected as shown below:

On the cover page, left column:

After "Assignee:" "Schering-Plough Corporation" should read ---

"Schering Corporation---."

Signed and Sealed this

Tenth Day of November, 1987

Attest:

DONALD J. QUIGG

*Attesting Officer*          *Commissioner of Patents and Trademarks*